United States Patent [19]

Gogolewski et al.

[11] Patent Number: 5,275,601
[45] Date of Patent: Jan. 4, 1994

[54] SELF-LOCKING RESORBABLE SCREWS AND PLATES FOR INTERNAL FIXATION OF BONE FRACTURES AND TENDON-TO-BONE ATTACHMENT

[75] Inventors: Sylwester Gogolewski, Alvaneu-Dorf; Stephan M. Perren, Davos, both of Switzerland

[73] Assignee: Synthes (U.S.A), Paoli, Pa.

[21] Appl. No.: 753,837

[22] Filed: Sep. 3, 1991

[51] Int. Cl.$^5$ .................................. A61B 17/56
[52] U.S. Cl. ............................ 606/72; 606/69; 606/73
[58] Field of Search ............ 606/69, 70, 71, 72, 606/73, 75, 76, 77, 78, 80; 411/185, 187, 188, 399

[56] References Cited

U.S. PATENT DOCUMENTS

| | | | |
|---|---|---|---|
| 213,551 | 3/1879 | Doten | 411/399 |
| 388,000 | 8/1888 | Rider | 411/399 |
| 1,151,861 | 8/1915 | Brumback | 411/399 |
| 2,136,524 | 11/1938 | Rosenberg | 411/187 |
| 3,741,205 | 6/1973 | Markolf | 606/73 |
| 4,655,661 | 4/1987 | Brandt | 411/399 |
| 4,776,329 | 10/1988 | Treharne | 606/77 |
| 4,905,680 | 3/1990 | Tunc | 606/77 |
| 5,019,078 | 5/1991 | Perren | 606/73 |
| 5,085,660 | 2/1992 | Lin | 606/73 |

FOREIGN PATENT DOCUMENTS

| | | | |
|---|---|---|---|
| 0742618 | 3/1933 | France | 606/69 |
| 1502020 | 8/1989 | U.S.S.R. | 606/69 |

*Primary Examiner*—Michael A. Brown
*Attorney, Agent, or Firm*—Davis Hoxie Faithful & Hapgood

[57] ABSTRACT

An absorbable bone screw and plate system with self-locking properties. The absorbable bone screw comprises a threaded shaft portion 1 for insertion into bone and a head portion 3 for rigid connection in the screw hole 13 of a bone plate 20, the diameter of said head portion 3 increasing in the direction opposite to the shaft portion 1, and the outer surface of said head portion 3 being provided with a three-dimensional structure 4 in the form of corrugations.

15 Claims, 6 Drawing Sheets

FIG. 4a
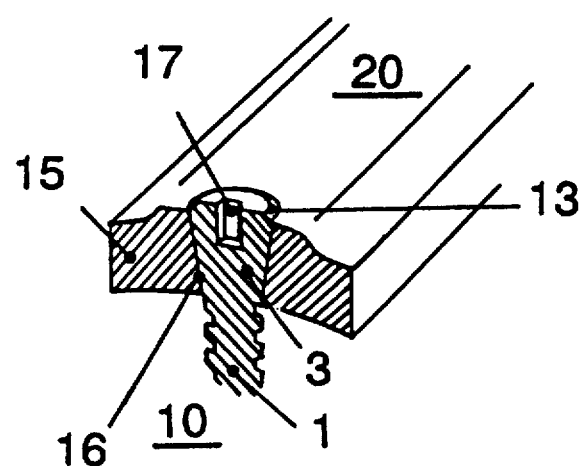
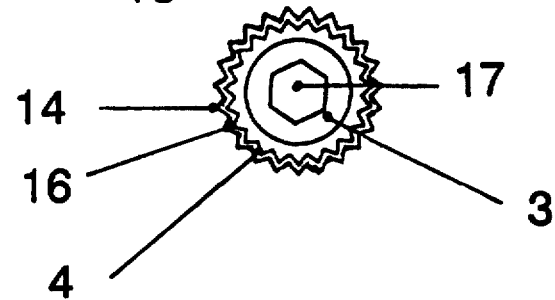
FIG. 4b

SELF-LOCKING RESORBABLE SCREWS AND PLATES FOR INTERNAL FIXATION OF BONE FRACTURES AND TENDON-TO-BONE ATTACHMENT

1. FIELD OF THE INVENTION

The present invention relates to bone screws and plates used for internal fixation of bone fractures, which are produced from a resorbable polymer and/or resorbable polymer-resorbable glass/ceramic composite which is finally resorbed and/or incorporated in the tissues.

Bone fractures are usually reduced using temporary internal and/or external fixation devices such as screws, plates, wires and external fixators.

2. DESCRIPTION OF THE PRIOR ART

Commonly used osteosynthesis devices are produced from metals, mainly from medical grade stainless steel, pure titanium or titanium alloys.

Metallic implants used successfully for fracture reduction also have certain disadvantages. They show large differences in Young's modulus as compared with moduli of bones, frequently undergo in vivo corrosion, and have to be removed after the bone fracture is healed.

To avoid these problems, numerous efforts have been undertaken to develop internal fixation devices which do not have to be removed from the implantation site, do not corrode, have Young's moduli close to those of the bone, transfer increasing load to the bone, and yet assure adequate fixation of bony fragments.

Materials which are considered as candidates for such implants are bioresorbable polymers and eventually resorbable polymers reinforced with resorbable glasses and/or ceramics.

The use of resorbable polymers for construction of internal fixation devices is the subject of numerous publications, e.g.:

Kulkarni RK, Pani KC, et al (1969), Polylactic acid for surgical implants, Arch Surg 93, 839;

Cutright DE, Hunsuck EE, et al (1971), Fracture reduction using a biodegradable material, polylactic acid, J Oral Surg 29, 393;

Vert M, Chabot F, et al (1981), Bioresorbable plastic materials for bone surgery, in Macromolecular Biomaterials, CRC Press, Boca Raton, 119;

Leenslag JW, Pennings AJ, et al (1987), Plates and screws for internal fracture fixation, Biomaterials 8, 70;

Tunc R (1990) Absorbable bone plate, U.S. Pat. No. 4,905,680, Mar. 6, 1990;

Matsusue Y, Yamamuro T, et al (1991), Biodegradable screw fixation of rabbit tibia proximal osteotomies, J Appl Biomat 2,1.

The main drawbacks of resorbable polymeric screws and plates developed at present are their relatively poor mechanical properties, and frequently, early loss of stability of fracture fixation. The latter is mainly observed with implants which are produced using methods which lead to at least partial orientation of a polymer. This seems to be due to loosening of the contact between the screw head and the plate hole, resulting from nonuniform swelling of the fixation elements in the body fluids, and the premature erosion of the screw thread, which in the majority of designs is a copy of the metallic screw thread.

Attempts have been made to protect against loosening of the contact between the screw head and the plate hole by welding both elements together. This technique is not an optimal one, however, as it changes the structure of a polymer in the heated zone, leading to thermal degradation of a polymer in the heat exposed area, and consequently, to a premature in vivo degradation of the welded area. It may also cause tissue necrosis due to the action of heat generated upon welding.

3. SUMMARY OF THE INVENTION

The present invention provides a resorbable bone screw and a bone plate system which allows the avoidance of the premature loosening of stability of the fracture fixation.

The contacting surfaces of the screw head and the plate hole are designed in such a way that after exposing the implants to the body fluids, the self-locking of the screw head in the plate hole is further enhanced.

This property has been achieved by constructing the screw head with a three-dimensionally structured, e.g. corrugated or serrated outer surface contacting the similarly structured surface of the plate hole.

Preferably the three-dimensional structure consists of at least two corrugations or serrations running around the outer surface of the head portion. The corrugated and/or serrated surface can have a symmetric and/or an asymmetric arrangement of corrugations/serrations. The angle between two consecutive corrugations/serrations should be in the range of 5° to 175°, and preferably 30° to 130°. The head portion of the bone screw according to the invention is preferably of conical or convex shape matching appropriate screw holes in the bone plate having a conical or concave shape, whereby the diameter of the screw hole is diminishing towards to bone contacting face of the plate.

Corrugations can run straight along the head, they can be of symmetrical, asymmetrical or spiral shape or they can combine these features.

The outer surface of the screw head can either be covered fully with corrugations or can be only partially covered by it, e.g. only in the upper, enlarged part of the screw head.

The dimensions of the corrugations/serrations will depend on the overall dimensions of the screw/plate system, but in general they will incise 1 to 50% of the screw head and preferably 5 to 10% of the screw head. The crest of the corrugations/serrations will be equal and/or 1 to 20% thinner and preferably 5 to 10% thinner than the crest of the screw head.

A suitable bone plate to be used together with the bone screw according to the invention may be made of the same or a similar resorbable polymer and/or resorbable polymer-resorbable glass/ceramic composite as the bone screw. The inner surface of the screw holes is provided with a three-dimensional structure corresponding to the three-dimensional structure on the outer surface of the head portion of the bone screw so that self-locking of the two three-dimensional structures (screw head/plate hole) occurs.

In a preferred embodiment of the bone plate it is provided with a continuous reinforcing bar portion running along the axis of the bone plate and accommodating the screw holes. The reinforcing bar portion is located at the upper part of the bone plate and has a height profile which diminishes from the lateral plate edges towards the center where the screw holes are located. By means of this design the overall stiffness of the bone plate is increased at the same time saving a considerable amount of material (in the lateral edge region of the bone plate). The bone plate with its reinforcing bar portion can be manufacture from one single piece of material or alternatively from two pieces one inferior plate component (with a rectangular profile) and a superior reinforcing bar component (with a trapezoid profile).

The thickness of the bone plate as measured across the reinforcing bar portion is preferably at least 1.1 to 2.0 times bigger than the thickness of the plate measured at the side edges of the plate, and most preferably 1.2 to 1.5 times thicker than the side edges of the plate.

In a further preferred embodiment of the bone plate its lower bone-contacting surface is at least partially provided with a three-dimensional structure, consisting e.g. of surface irregularities in the form of conical microcraters or pyramids. These when in contact with bone, will diminish the negative effect of the plate on the blood supply to the bone area under the plate. The three-dimensional structure at the bone-contacting surface of the plate may alternatively consist of undercuts, which preferably run parallel to its longitudinal axis.

The bone screw and plate of the present invention is fabricated from a resorbable polymer which can be processed into implants using injection-moulding, compression-moulding, extrusion and other techniques used for polymers processing. For certain applications the gel-processing will be preferable to melt-processing as it does not cause polymer degradation.

The dimensions of the screw and plate will depend on the areas of application (maxillofacial/small fragments/long bone/tendon surgery) and in general, are similar to those of existing metallic devices.

When used in situations allowing accommodation larger implants, the implants of the invention will have dimension larger than conventional ones to compensate for differences in mechanical properties between metals and polymers.

The number of the corrugated/serrated screw holes in the plate is similar to that of metallic implants, although it may be necessary to increase the number of holes when the implant is used in the area of increased load.

Implants of the invention are preferably produced from oriented or at least partially oriented resorbable polymers, which means that they will have a fibrillated structure, at least in the surface (skin) layer formed upon processing.

In a preferred embodiment of the invention the crest of the bone screw thread has 0.11 to 1.00 mm thickness, and preferably 0.12 to 0.50 mm thickness which is at least 0.01 to 5.00 times thicker than the crest of metallic cancellous/cortex bone screws, or standard metallic screws with metric (ISO) or English (ANSI) thread, and preferably 0.5 to 1.0 times thicker than the crest of such screws.

The use of a thread thickness typical for metallic screws in the resorbable screws, would result in premature erosion of the crests, and thus the loss of stability of bone fracture fixation.

The implants of the invention can be used in typical situations when bone screws and plates are used, but they can also be used for attachment of tendon to the bone in the case of tendon fracture (e.g. disrupted tendon of the rotator cuffs).

Typical resorbable polymers suitable for fabrication of the devices of the invention are listed in Table I. It should be stressed, however, that the table lists only commercially available polymers and is far from being complete.

TABLE I

Typical examples of resorbable materials for constructing the devices of the invention:

Polyhydroxyacids, e.g. poly(L-lactide, poly(D-lactide), poly(L/D-lactide), poly (L/DL-lactide), polyglycolide, copolymers of lactide and glycolide of various compositions, copolymers of said lactides and/or glycolide with other polyesters, copolymers of glycolide and trimethylene carbonate, polyhydroxybutyrate, polyhydroxyvalerate, copolymers of hydroxybutyrate and hydroxyvalerate of various compositions, polyorthoesters, polyanhydrides, polydioxanone, polydioxanediones, polyesteramides, polymalic acid, polyesters of diols and oxalic and/or succinic acids, polyaminoacids, copolymers of amino acids and glutamic acid, polyamides, polycaprolactone, polycarbonates.

Preferred degradable polymers (homopolymers/copolymers) are polylactides, polyglycolide, polydioxanone, poly/glycolide-co-trimethylene carbonate), poly(lactide-co-glycolide), and polyesteramides.

Molecular weight of resorbable polymers to be used for fabrication of devices of the invention should be in the range of 50.000 to 1.000.000 and preferably in the range of 120.000 to 600.000 (viscosity-average molecular weight) as calculated from the following formula:

$$[\eta] = 5.45 \times 10^{-4} M_v^{0.73}$$

These polymers can also be used with admixture of small amounts of tricalcium phosphate and/or hydroxyapatite, added to a polymer before processing.

4. BRIEF DESCRIPTION OF THE DRAWINGS

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

In the drawings,

FIG. 1b is a partial side view of the head portion of the screw according to FIG. 1a;

FIG. 4a is a cross-sectional view of the bone screw according to FIG. 1 fitting the bone plate according to FIG. 2;

FIG. 4b is a partial top view of the screw/bone-plate system according to FIG. 4a;

FIG. 5b is an enlarged detailed perspective view of the three-dimensional irregularities located at the undersurface of the bone plate according to FIG. 5a.

5. DESCRIPTION OF THE PREFERRED EMBODIMENTS

Figure 1A:
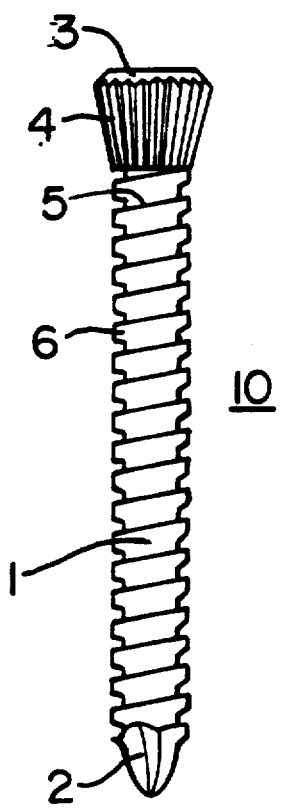
FIG. 1a is a side view of one of the embodiments of the bone screw of the present invention.

The bone screw according to the invention and the corresponding bone plate are now further described by having reference to the drawings:

As shown in FIG. 1a the absorbable bone screw 10 according to the invention basically comprises a threaded shaft portion 1 with a pointed end 2 for insertion into bone and a head portion 3 for rigid connection in the screw hole of a bone plate. The diameter of the head portion 3 increases over the full length of the head portion 3 in the direction opposite to said shaft portion 1 such as to form a frustum of a cone. The outer surface of the head portion 3 is provided over its full circumference with a three-dimensional structure 4 forming a symmetric, corrugated surface. The elevations and depressions of the corrugations are running from the top of the head portion 3 (having a larger diamter of approximately 5 mm) to the lower part of the head portion 3 (having a smaller diameter of approximately 3 mm).

Figure 1B:
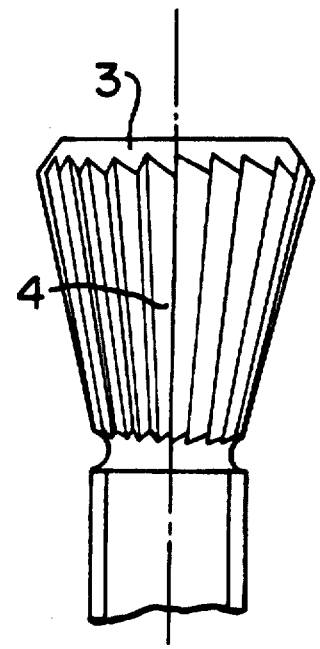
Figure 1C:
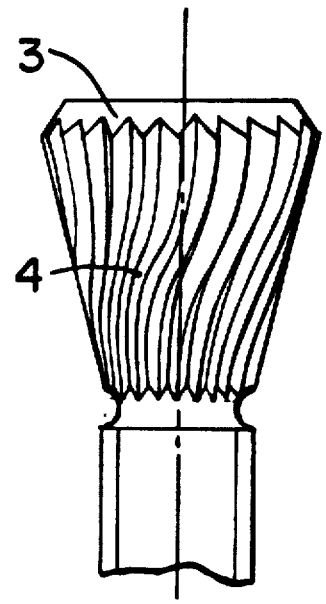
FIG. 1c is a side view of a modified head portion of the bone screw of the present invention.

FIGS. 1b and 1c are representing modifications of the three-dimensional structure 4 of the outer surface of the head portion 3 (FIG. 1b: asymmetric, corrugated surface/ FIG. 1c: spiral-shaped, corrugated surface). The thread 5 of the shaft portion 3 is provided with crests 6 having 0.2 mm thickness.

Figure 2:
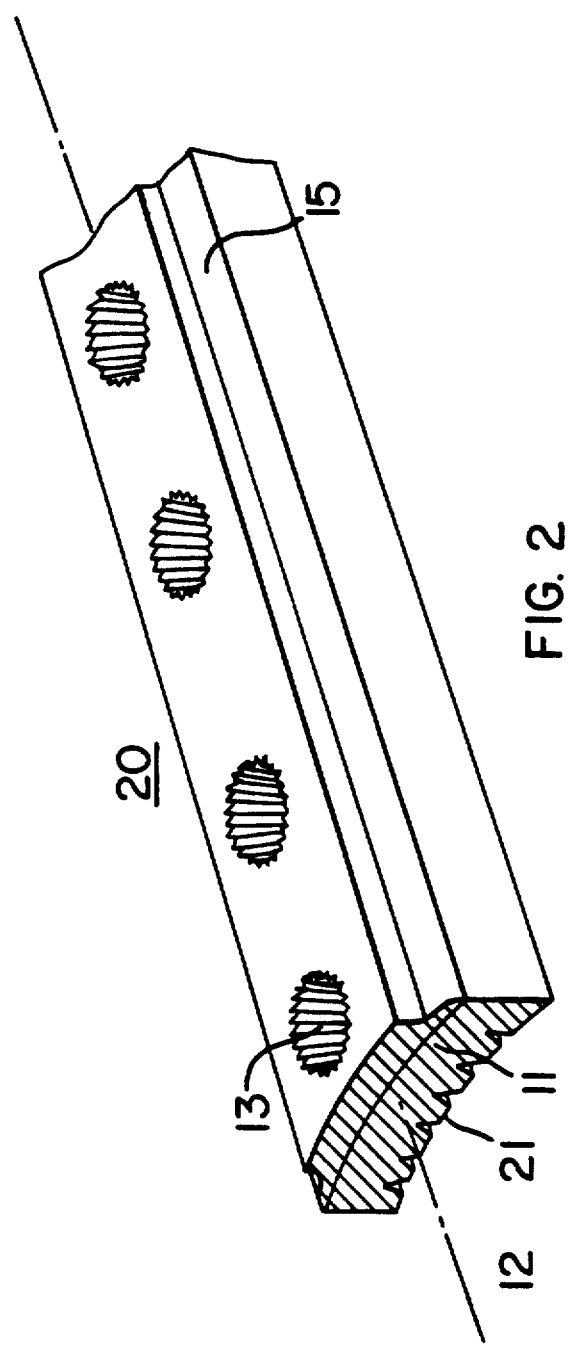
FIG. 2 is a perspective view of the bone plate with corrugated/serrated screw holes and reinforcing bar.

The corresponding bone plate 20 to be used with the bone screw 10 is shown in FIG. 2. It has a length of approximately 50 mm and a width of 7 mm. Its profile 11 is approximately rectangular in its inferior part (bone contacting side) and approximately trapezoidal in its superior part. Along its longitudinal axis 12 a plurality of screw holes 13 are located for receiving absorbable bone screws 10. The screw holes 13 have the shape of a frustum of a cone in order to match the correspondingly shaped head portion 3 of the bone screws 10 to be inserted therein. The larger diameter of the screw hole 13 of approximately 5 mm is located at the upper side of the bone plate 20 and the smaller diameter of the screw hole 13 of approximately 3 mm is located at the lower (bone-contacting) side of the bone plate 20. The resorbable plate 20 has a reinforcing bar portion 15 running longitudinally along the plate 20 and accommodating the screws holes 13. The thickness of the plate 20 as measured across the reinforcing bar portion 15 is 5 mm and the thickness of the plate 20 measured at the side edges of the plate 20 is 3 mm.

Figure 3:
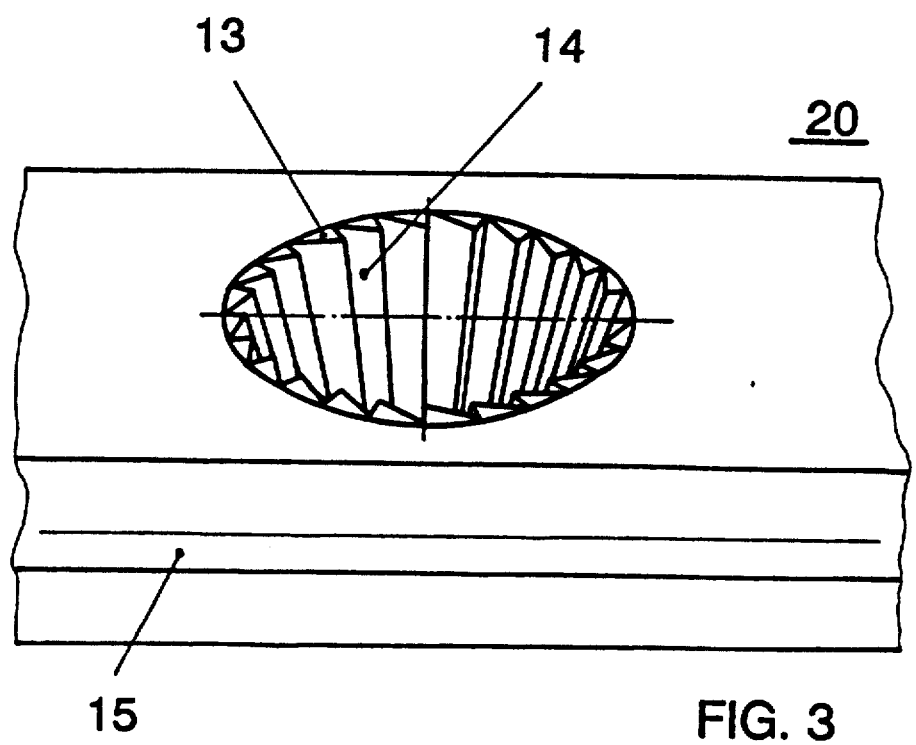
FIG. 3 is an enlarged partial view of a corrugated/serrated screw hole of the bone plate according to FIG. 2.

As shown in FIG. 3 the inner surface of the screw holes 13 is provided with a three-dimensional structure 14 corresponding to the three-dimensional structure 4 on the outer surface of the head portion 3 of the bone screws 10, so that self-locking of said two three-dimensional structures 4 and 14 occurs upon insertion of the bone screw 10 into the screw hole 13.

FIG. 4 shows in detail how the conical head portion 3 of the bone screw 10 fits into the screw hole 13 of the bone plate 20 and interlocks with it in the interlocking zone 16. In order to facilitate insertion of the bone screw 10 a hexa-hole 17 is provided in the head portion 3.

Figure 5A:
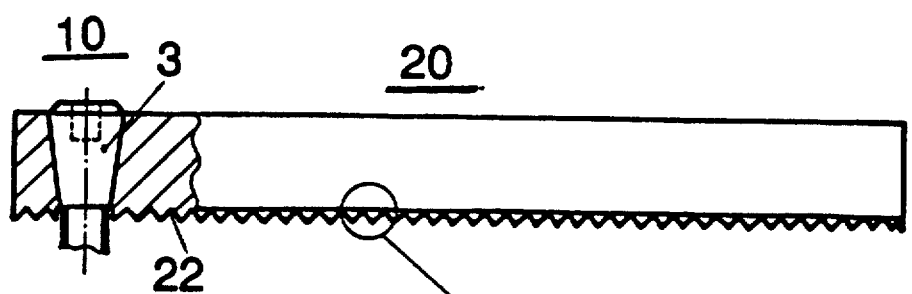
FIG. 5a is longitudinal section through a modified screw/bone plate system according to FIG. 4 with a three-dimensionally structured undersurface.
Figure 5B:
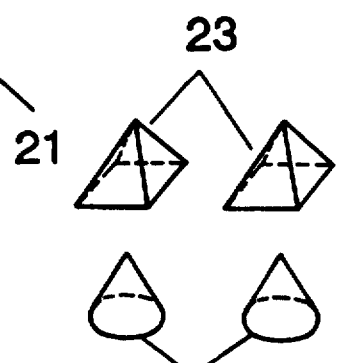

In a preferred embodiment of the invention—represented in FIGS. 5a and 5b—the lower surface 22 of the bone plate 20 is provided with a regular three-dimensional structure 21 consisting of conical elements 23 or pyramidal elements 24 designed to decrease the contact area between the plate 20 and the bone. The lower surface 22 of the bone plate 20 may be further provided with undercuts (not represented in the figure), preferably running parallel to its longitudinal axis.

Figure 6:
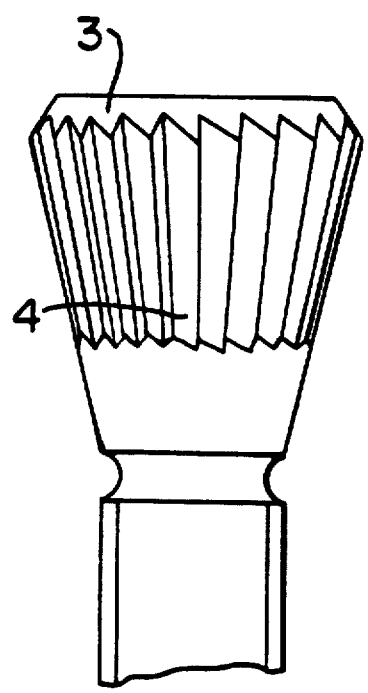
FIG. 6 is a side view of another embodiment of the bone screw of the present invention.

In a further preferred embodiment of the invention—represented in FIG. 6—the outer surface of the conical head portion 3 of the bone screw 10 is provided only in its upper part with a three-dimensional structure 4 in the form of corrugations running around the full circumference of the head portion 3.

We claim:

1. A bone screw comprising a shaft portion having a thread for insertion into bone and a head portion for rigid connection in a screw hole of a bone plate, the diameter of said head portion increasing in the direction opposite to said shaft portion over at least a portion of the length of said head portion and at least a part of the outer surface of said head portion having a three-dimensional structure, said thread of said shaft portion having crests from 0.11 to 1.00 mm in thickness, and said screw being made of a material capable of absorption by body tissue.

2. An absorbable bone screw according to claim 1 in which the thread of said shaft portion is provided with crests having 0.12 to 0.50 mm thickness.

3. An absorbable bone screw according to claim 1 in which said head portion is conical.

4. An absorbable bone screw according to claim 1 in which said head portion is convex.

5. An absorbable bone screw according to claim 1 in which said three-dimensional structure consists of corrugations or serrations running around said outer surface of said head portion.

6. An absorbable bone screw according to claim 5 having at least two corrugations or serrations.

7. An absorbable bone screw according to claim 1 in which said three-dimensional structure is limited to the upper part of said outer surface of said head portion.

8. An absorbable bone screw according to claim 1 produced from oriented or at least partially oriented resorbable polymers.

9. An absorbable bone screw according to claim 8 in which at least the surface layer of said bone screw has a fibrillated structure.

10. An absorbable bone plate with an upper surface, a lower surface for contacting bone, a longitudinal axis and a plurality of screw holes located along said axis for use with an absorbable bone screw having a head portion and a shaft portion, said head portion having an outer surface being a three dimensional structure running generally in the longitudinal direction, wherein said head portion increases in diameter in the direction opposite to said shaft portion, in which the inner surface of said screw holes is provided with a three-dimensional structure running generally longitudinally in the direction of the screw holes' axes corresponding to said three-dimensional structure on said outer surface of said head portion of said bone screw to permit self-locking of said two three-dimensional structures.

11. An absorbable bone plate according to claim 10 comprising at least one reinforcing bar running along said axis of the plate and accommodating the screw holes.

12. An absorbable bone plate according to claim 10 which said lower surface is at least partially provided with a three-dimensional structure.

13. An absorbable bone plate according to claim 12 in which said three-dimensional structure comprises conical or pyramidal elements designed to decrease the contact area between the plate and the bone.

14. An absorbable bone plate according to claim 10 in which said lower surface is provided with undercuts, which preferably run parallel to said longitudinal axis.

15. A bone screw/bone plate system comprising
a plurality of absorbable bone screws having a threaded shaft portion for insertion into bone and a head portion for rigid connection in the screw hold of a bone plate, said screw hole having an axis, the diameter of said head portion increasing in the direction opposite to said shaft portion over at least a portion of the length of said head portion and in which at least a part of the outer surface of said head portion has a three-dimensional structure; and
an absorbable bone plate with an upper surface, a lower surface for contacting bone, a longitudinal axis and a plurality of screw holes located along said longitudinal axis for receiving said absorbable bone screws, said screws holes having three-dimensional structure running generally in the direction of the screw hole axis.

* * * * *

UNITED STATES PATENT AND TRADEMARK OFFICE
CERTIFICATE OF CORRECTION

PATENT NO. : 5,275,601
DATED : January 4, 1994
INVENTOR(S) : Gogolewski et al.

It is certified that error appears in the above-identified patent and that said Letters Patent is hereby corrected as shown below:

Col. 7, line 14, (Claim 15) cancel "hold" and substitute --hole--.

Signed and Sealed this

Twenty-sixth Day of July, 1994

Attest:

BRUCE LEHMAN

Attesting Officer     Commissioner of Patents and Trademarks